United States Patent [19]

Warren

[11] Patent Number: Plant 7,529

[45] Date of Patent: May 21, 1991

[54] MAPLE TREE NAMED 'KEITHSFORM'

[75] Inventor: Keith S. Warren, Gresham, Oreg.

[73] Assignee: J. Frank Schmidt & Son Co., Boring, Oreg.

[21] Appl. No.: 461,539

[22] Filed: Jan. 5, 1990

[51] Int. Cl.[5] ..... A01H 5/00

[52] U.S. Cl. ..... Plt./51

[58] Field of Search ..... Plt./51

*Primary Examiner*—James R. Feyrer

*Attorney, Agent, or Firm*—Klarquist, Sparkman, Campbell, Leigh & Whinston

[57] ABSTRACT

A novel *Acer truncatum* tree characterized by its rapid rate of growth, its straight trunk, branches of two year trees which are extremely symmetrical and of substantially equal length and which angle from the trunk at approximately forty five degrees, a brilliant red autumn color which is initiated relatively late in the fall, and a relatively large leaf size.

1 Drawing Sheet

The present invention relates to a new and distinct variety of maple tree of the species botanically known as *Acer truncatum.* I have named my new variety "Keithsform".

I discovered my new variety as a seedling mutation or chance seedling of unknown parentage in a group of *Acer truncatum* seedlings being grown in a cultivated area of the J. Frank Schmidt & Son Co. Nursery in Boring, Oreg. My attention was first directed to the new plant because of its atypically large leaves. I further observed the brilliant red fall color of this tree. Further observation of this plant convinced me that it was quite unusual and distinct from other *Acer truncatum* seedlings. Although the parentage of my new variety of tree is uncertain, its features lead me to suspect that *Acer platanoides* is the pollen parent.

Close observations of the new seedling and continued observations of progeny thereof, subsequently asexually propagated under my direction by budding onto *Acer platanoides* rootstock (with which it is quite compatible) as well as by rooting softwood cuttings, has confirmed that the unique characteristics of my new variety is a result of a seedling variation. I am therefore convinced that my new tree represents a new and improved variety of *Acer truncatum,* as particularly evidenced by the following unique combination of characteristics, which have proven firmly fixed, are outstanding therein, and which distinguish it from all other varieties of this species:

1. Rapid rate of growth;
2. A unique habit of growth resulting in a very straight trunk, a symmetrical branch structure of two year old trees with all branches being nearly equal in length; and branches which extend at a very uniform branch angle from the trunk;
3. Fall colors which are initiated relatively late and leaves which are retained relatively long into the fall; and
4. In comparison to standard *Acer truncatum* trees, a larger leaf, a greater number of small lobes per leaf, larger stem thickness, a longer internode length, improved branching in the nursery, and a brighter shade of fall color; and
5. Dormant buds which are a reddish-brown.

The accompanying photographs depict the color of the foliage of my new variety as nearly true as is reasonably possible to make the same in a color illustration of this character.

FIG. 1 is a color photograph of a two year old tree of the present invention.

FIG. 2 is a color photograph of a group of one year old trees of the present invention.

FIG. 3 is a color photograph of leaves of the tree of the present invention showing their autumn colors.

One of the primary distinguishing features of my new tree over other trees of this species is its rate and habit of growth. From a comparison of the characteristics of a number of trees of my new variety with those of both the standard *Acer truncatum* and *Acer platanoides* varieties growing under comparable conditions in the J. Frank Schmidt & Son Co. Nursery, I have observed that my new variety at one year has grown much faster than *Acer truncatum* trees but at a rate slightly less than *Acer platanoides* trees. However, one year trees of my new variety have far more branches which are longer than 6 inches than either the *Acer truncatum* or *Acer platanoides* varieties. Table I below sets forth the results of a comparison of, and averaging measurements of, characteristics of 10 one year old trees of my new variety, ten *Acer truncatum* seedling trees and 10 *Acer platanoides* trees.

TABLE I

| | 1 YEAR NURSERY TREES | | |
|---|---|---|---|
| Characteristic | New Variety | Seedling *Acer truncatum* | *Acer platanoides* |
| Height: | 241 cm | 144 cm | 259 cm |
| Number of branches longer than 6 inches: | 12.8 | 0 | 3.5 |
| Branches per meter of height: | 5.3 | 0 | 1.35 |
| Length of unbranched leader above top branch | 66 cm | No branches | 183 cm |

A comparison of leaves of my new variety with leaves of seedling *Acer truncatum* trees and of *Acer platanoides* trees has revealed that leaves of my new variety are much larger and have more pointed sublobes per leaf than the leaves of seedling *Acer truncatum* trees, but are smaller and have fewer sublobes per leaf than *Acer platanoides* trees. Also, the leaves of my new variety have smoother margins and surface textures and a higher gloss than those of *Acer platanoides* trees, but are less glossy than leaves of standard *Acer truncatum* trees.

A comparison of these leaf characteristics, with sizes and number of lobes being averages, between leaves of my new variety, those of standard *Acer truncatum* trees and those of *Acer platanoides* trees is set forth below in Table II.

TABLE II

| | New Variety | *A. truncatum* | *A. platanoides* |
|---|---|---|---|
| Leaf Width | 13.3 cm | 8.0 cm | 15.0 cm |
| Leaf Length | 18.1 cm | 9.5 cm | 21.0 cm |
| Pointed sublobes per leaf: | 6.7 | 3.7 | 19.0 |
| Leaf Margin: | Smooth to slightly wavy | Smooth | Wavy |
| Surface Texture: | Smooth | Smooth | Wrinkled |
| Leaf Surface Sheen: | Moderately glossy | Glossy | Dull |
| Leaf Pubescence, Underside: | Moderate in axils of palmate veins, little or none in axils of secondary veins. | Slight in main palmate vein vein axils only. | Moderate in axils of main and secondary veins. |
| Petioles: | Slender, 55:1 length to width ratio | Slender, 53:1 length to width ratio | Stout, 40:1 length to width ratio |

In addition, the dormant buds of my new variety are greyed-orange (177c) becoming greyed-purple (187c) and are of a medium size (4–6 mm) in comparison to the greyed-red (178a) becoming greyed-orange (174a), small (1.5–2.0 mm) and flat dormant buds of standard *Acer truncatum* trees and the green (143c) becoming greyed-purple (183a), 4–7 mm plump buds of *Acer platanoides* trees. In addition, the bark of two year old trees of my new variety is brown and slightly rough. In contrast, the bark of similar age trees of standard *Acer truncatum* trees and *Acer platanoides* trees are, respectively, brown and rough; and greenish-brown and smooth. In addition, a measurement of the internode length at 30 cm below the terminal of a number of trees of my new variety reveal this length to be 7 cm on average while a comparable measurement of the internode length of standard *Acer truncatum* and *Acer platanoides* trees reveal the length to be 4 cm and 11 cm, respectively.

Trees of my new variety have a summer leaf color which is yellow/green to green (like RHS 147B to RHS 137a) and a brilliant red fall color (like RHS 42a, 46a and 44b). By comparison, typical *Acer truncatum* trees have a yellow/green summer color (like RHS 144a, 146b and 147a) and a gray/purple fall color (like RHS 183b to 184a and 187a). As a further comparison, *Acer platanoides* trees typically have a green summer color (like RHS 137b and 139b) and a yellow/orange fall color (like RHS 20a to 21b).

Otherwise, so far as I have observed at this time, my new variety is generally typical of the species.

The following is a detailed description of my new variety of "Keithsform" *Acer truncatum* tree, with color terminology in accordance with the Royal Horticulture Society Colour Chart (hereinafter RHS), published by The Royal Horticultural Society of London.

Parentage: A seedling mutation or chance seedling of unknown parentage, but which is believed to have *Acer platanoides* trees as the pollen parent.

Propagation: Holds to distinguishing characteristics through succeeding propagation by budding and rooting of softwood cuttings.

Location where grown and observed: J. Frank Schmidt & Son Co. Nursery in Boring, Oreg.

Tree: Raidly growing with a very straight trunk.

Branches: Symmetrical branch structure as a two year old tree; with all branches being nearly equal in length and extending from the trunk at an angle of approximately forty five degrees.

Foliage:

*Shape.*—Palmate, five main lobes per leaf with typically about seven pointed sub-lobes per leaf.

*Leaf size.*—Length, typically about 18 cm; breadth, typically about 13 cm.

*Margin.*—Smooth to slightly wavy.

*Surface texture.*—Smooth.

*Apex.*—Acuminate.

*Base.*—Rounded to cordate.

*Pubescence.*—Underside of leaf, moderate in axils of main palmate veins, little or none in axils of secondary veins.

*Leaf surface sheen.*—Moderately glossy.

*Main veins, leaf underside.*—Raised.

*Small veins, leaf underside.*—Slightly raised.

*Petioles.*—Slender.

*Color.*—As described above and more specifically: the leaf summer color is yellow/green (like RHS 147b) to green (like 137a). In the fall, the leaves turn to a brilliant red color (like red RHS 42a, red RHS 46a, and red RHS 44b).

*Dormant buds.*—Greyed-orange (177C) becoming greyed-purple (187B), medium size, 4–6 mm.

*Bark, 2 year trunk.*—Greyed-orange (like RHS 165C), slightly rough.

*Internode length, measured at 30 cm below terminal.*—About 7 cm.

*Fall changes.*—As described above, under typical Oregon conditions, somewhat later than most *Acer truncatum* trees, with initial color occurring about November 5th and peak color occurring about November 15th–20th. My new variety retains its colored leaves somewhat longer into the fall than other *Acer truncatum* trees, with leaves falling typically about November 30th.

I claim:

1. A new and distinct variety of *Acer truncatum* tree, substantially as herein shown and described, characterized particularly as to novelty by its rapid rate of growth, its very straight trunk, branches of one year trees which are extremely symmetrical; and of substantially equal length and which angle from the trunk at approximately forty five degrees, a brilliant red autumn color which is initiated relatively late in the fall, and a relatively large leaf size.

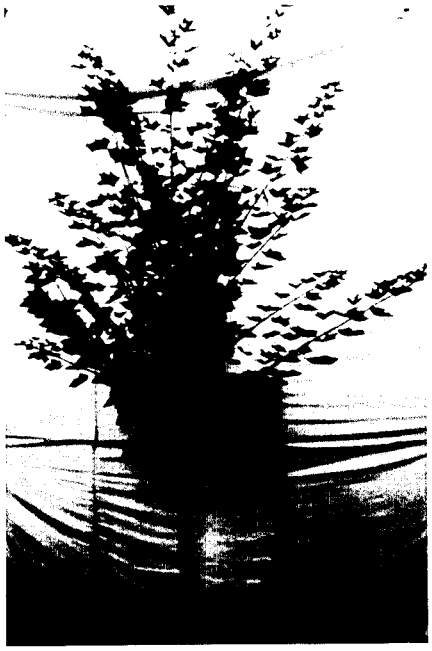
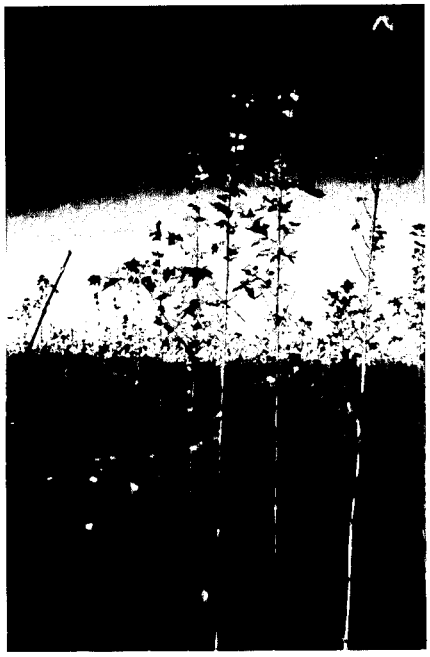
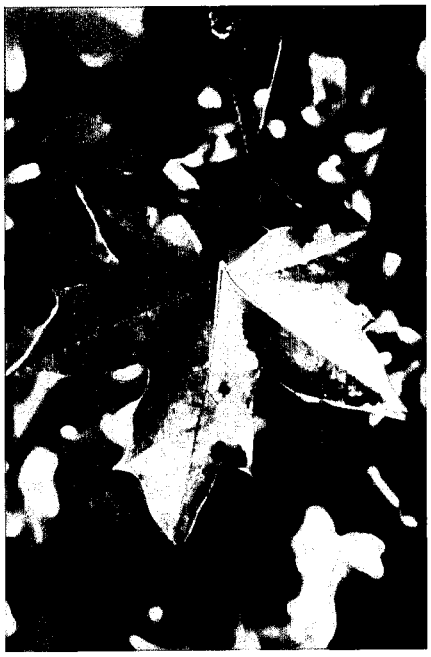

* * * * *